United States Patent [19]

Duffy et al.

[11] Patent Number: 6,020,367

[45] Date of Patent: Feb. 1, 2000

[54] SUPERSATURATED ASCORBIC ACID SOLUTIONS

[75] Inventors: John A. Duffy, West Milford; Dmitri Ptchelintsev, Mahwah, both of N.J.

[73] Assignee: Avon Products, Inc., New York, N.Y.

[21] Appl. No.: 08/982,821

[22] Filed: Dec. 2, 1997

[51] Int. Cl.[7] .............................. A61K 6/00; A01N 43/08
[52] U.S. Cl. .................. 514/474; 549/315; 424/401; 424/450; 424/490; 424/489; 514/262; 514/263; 514/264; 514/440; 514/456; 514/457
[58] Field of Search ............................. 549/315; 514/474, 514/262, 263, 264, 440, 456, 457; 424/450, 490, 401

[56] References Cited

U.S. PATENT DOCUMENTS

| | | | |
|---|---|---|---|
| 2,132,662 | 10/1938 | Volwiler et al. | 260/501 |
| 2,134,246 | 10/1938 | Elger | 23/250 |
| 2,150,140 | 3/1939 | Warnat | 260/344 |
| 2,179,978 | 11/1939 | Elger | 260/344 |
| 2,297,212 | 9/1942 | Gockel | 99/11 |
| 4,254,105 | 3/1981 | Fukuda | 424/170 |
| 4,767,750 | 8/1988 | Jacquet et al. | 514/159 |
| 4,828,837 | 5/1989 | Uster et al. | 424/450 |
| 4,960,764 | 10/1990 | Figueroa, Jr. et al. | 514/63 |
| 5,120,762 | 6/1992 | Hanaoka et al. | 514/474 |
| 5,308,621 | 5/1994 | Taylor et al. | 424/401 |

FOREIGN PATENT DOCUMENTS 375573  8/1938  Canada .

*Primary Examiner*—Frederick Krass
*Attorney, Agent, or Firm*—Ohlandt, Greeley, Ruggiero & Perle, LLP

[57] ABSTRACT

A method of preparing a supersaturated and stable solution of ascorbic acid, supersaturated ascorbic acid solutions and compositions containing such supersaturated solutions. A polyol vehicle is heated to an elevated temperature, and the ascorbic acid is dissolved therein to form an ascorbic acid/polyol solution. The method provides a solution containing a significant concentration of ascorbic acid that is stable over time, temperature changes and other environmental factors.

21 Claims, No Drawings

SUPERSATURATED ASCORBIC ACID SOLUTIONS

BACKGROUND OF THE INVENTION

1. Field of the Invention

The present invention relates to supersaturated solutions of ascorbic acid and compositions including such solutions. In addition, the present invention relates to supersaturated, yet stable, solutions of L-ascorbic acid and/or other physiologically acceptable isomers of ascorbic acid. More specifically, the invention relates to a chemically stable L-ascorbic acid and its isomeric forms, in solution, at very high concentration levels. The present invention further provides a method of forming chemically stable, supersaturated ascorbic acid solutions.

2. Description of the Prior Art

L-ascorbic acid (vitamin C) is a water-soluble, "red-ox" (reduction-oxidation) active carbohydrate. Physiologically, L-ascorbic acid functions as a reductive cofactor for enzymes that require transition metal ions in reduced form (such as $CU^+$ and $Fe^{+2}$) for optimum activity. Such enzymes include proline and lysine hydroxylases that are responsible for proper structure and function of skin collagen and elastin. This red-ox cofactor role is one mechanism by which L-ascorbic acid contributes to the maintenance of proper structural and functional integrity of tissues, such as in the epidermal and dermal layers of human skin. *J. Soc. Cosmet. Chem.*, vol. 34, pages 439–451 (1983).

The red-ox properties of L-ascorbic acid also make it a good scavenger of reactive radicals, such as superoxide $0^{-2}$, hydroxyl $HO^-$, peroxyl $ROO^-$ and alkoxyl $RO^-$ radicals. Such reactive radicals are generated in skin upon exposure to ultraviolet light or chemical initiators, such as singlet oxygen, ozone and peroxides. It has been found that by scavenging such reactive radicals, L-ascorbic acid protects the skin against oxidative damage and reduces consequent photoaging symptoms, such as dryness, wrinkling, irregular pigmentation and loss of elasticity. *Advances in Free Radical Biology and Medicine*, vol. 2, pages 419–444 (1986); *British J. Dermatol.*, vol. 127, pages 247–253 (1992).

Despite its hydrophilic nature, L-ascorbic acid also has the ability to help regenerate the lipophilic antioxidant, tocopherol (vitamin E), from corresponding tocopheroxyl radicals. *Chemistry Letters*, vol. 6, pages 789–792 (1982). By regenerating tocopherol, L-ascorbic acid helps preserve the skin's endogenous, antioxidant defense mechanisms.

Because of the numerous beneficial properties attributed to L-ascorbic acid, its topical use is desired. However, the formation of a topical delivery system for L-ascorbic acid is difficult since L-ascorbic acid is stable only in solid form and at ambient temperatures. L-ascorbic acid decomposes in solubilized form, undergoing rapid and irreversible aerobic and anaerobic degradation. *Int'l. J. Vit. Research*, Suppl. vol. 27, pages 259–306 (1985); *Bulletin Chem. Soc. Japan*, vol. 46, pages 902–904 (1973).

Both aerobic and anaerobic degradation reduces the efficacy of ascorbic acid products. Known topical delivery systems that contain such degraded L-ascorbic acid have poor aesthetic qualities due to discoloration, undesired changes in viscosity, malodor and evolution of carbon dioxide gas bubbles. Decomposition of L-ascorbic acid in solution has virtually precluded its use in personal care products at meaningful and effective concentrations. Therefore, manufacturers are currently forced to add only ineffective amounts of L-ascorbic acid to topical products just to meet the demand in the market for products containing L-ascorbic acid.

The following reaction sequence shows the typical aerobic degradation of L-ascorbic acid:

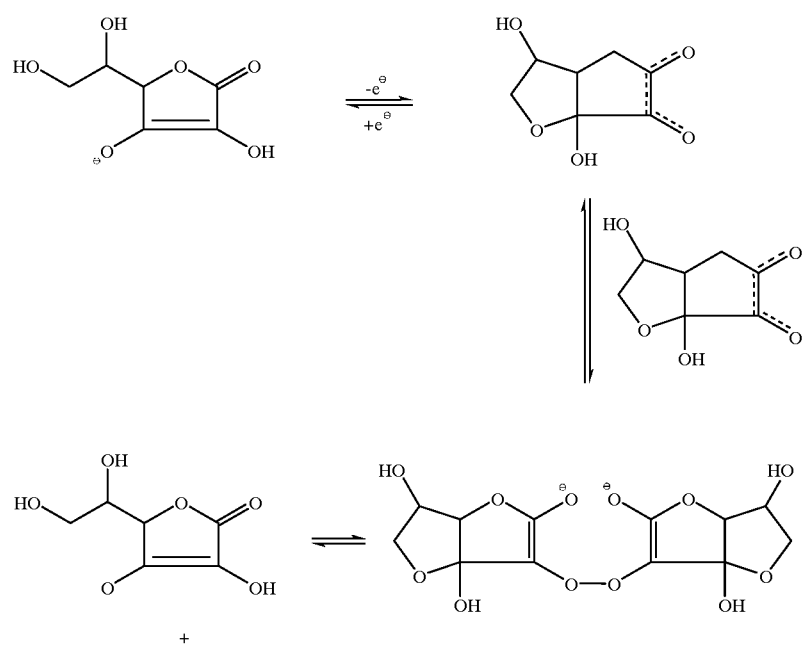

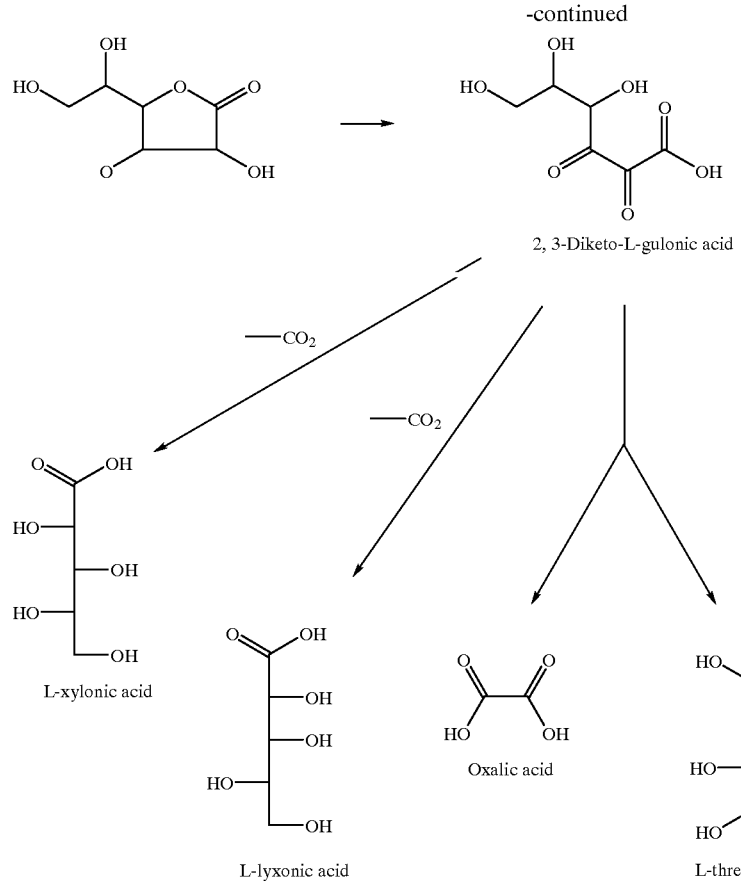

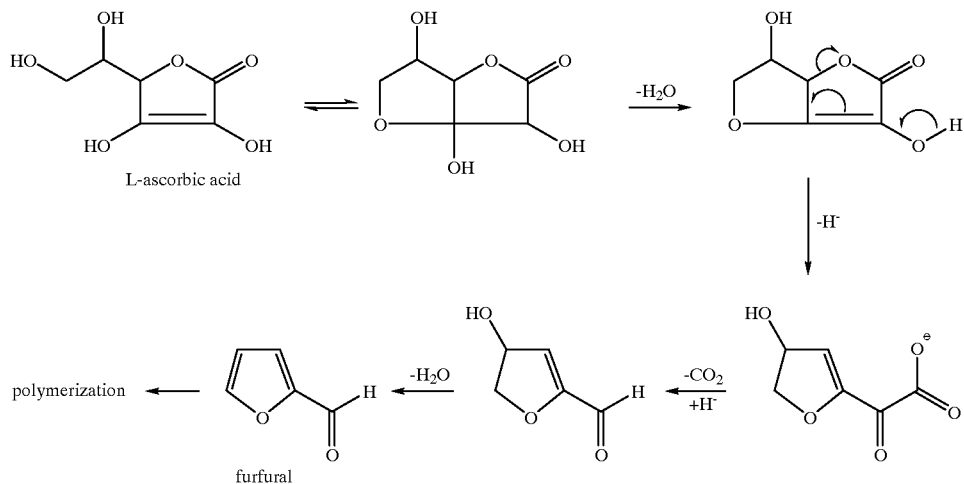

The following reaction sequence shows the anaerobic degradation of L-ascorbic acid:

Attempts have been made to obtain stable solutions of L-ascorbic acid. For example, U.S. Pat. No. 2,179,978 to Elger describes solutions of L-ascorbic acid in anhydrous ethanol. The application to the skin of L-ascorbic acid dissolved in a water-free, undiluted alcohol solution, such as ethanol, is not practical since the alcohol contributes to dryness and chapping of the skin and, thus negates the positive effect of L-ascorbic acid.

Another attempt at stabilizing L-ascorbic acid in solution involved adding a sulfur-containing reducing agent, such as sulfur dioxide, sulfur-containing acids and/or salts capable of emitting sulfur dioxide. However, the emission of sulfur dioxide causes a pungent and very disagreeable odor that simulates rotting eggs.

L-ascorbic acid at a concentration of less than 0.5 percent by weight has been reported as having been added to ethanol, glycerin, propylene glycol, sorbitol, dextrose, sucrose and corn sugar. *J. American Pharm. Assoc.*, vol. XLIV(4), page 241 (1955); *Yakugaku Zashi (Japan)*, vol. 96(2), page 232 (1976). At such a concentration, L-ascorbic acid provides no significant benefits to skin. One reason for the use of such a low concentration of L-ascorbic acid is that using current technology more L-ascorbic acid could not be dissolved in such a media and maintained without precipitation of ascorbic acid.

U.S. Pat. No. 5,120,762 to Hanaoka et al. is directed to a stable sodium ascorbate powder. However, such a powder forms an unstable solution. It has also been reported that the addition of phenolic antioxidants, such as rutin, quercetrin, quercetin, methylchalcone and hesperidin, to L-ascorbic acid may stabilize L-ascorbic acid in solution (*Referat Zhur. Khim., Biol. Khim.*, Abstract No. 1635 (1960). The reported stabilizing effects are questionable since phenolic antioxidants form colors in solution that indicate instability. Further, colored solutions are not aesthetically suitable for topical compositions.

Other additives that have been used in an effort to stabilize L-ascorbic acid in solution include oxalic acid, metaphosphoric acid, glutathione, thiourea and sodium diethyldithiocarbamate, *Can. J. Research*, vol. 28E, pages 19–32 (1950); proteins, *Biochimie*, vol. 56, page 1255–1267 (1974); and glycosaminoglycans, *Int. J. Pharmaceut.*, vol. 107, pages 199–203 (1994).

Other attempts at stabilizing solutions of L-ascorbic acid have included the addition to L-ascorbic acid of calcium salt of quinic acid (Swiss Patent No. 2,140,989); benzoyl and veratroyl esters (U.S. Pat. No. 2,150,140); ester of histidine (U.S. Pat. No. 2,134,246); salts of iron, manganese, calcium, bismuth, arsenic, silver, gold, mercury, copper, zinc, aluminum or tin (Canadian Patent No. 375,573); aliphatic amine esters (U.S. Pat. No. 2,132,662); thiourea and the methyl and ethyl derivatives of thiourea (U.S. Pat. No. 2,297,212); and thioglycolic or thiolactic acid (Japanese Patent Application No. 5048). Efforts have even included sealing L-ascorbic acid solutions under nitrogen in vacuum ampoules sterilized with phenol. *J. American Pharm. Assoc.*, vol. 35, page 363 (1946). The above attempts at providing a practical, aesthetically acceptable, stable, topical L-ascorbic acid in solution in which chemicals and bioactives are added to L-ascorbic acid, all have been unsuccessful.

Thus, the problem of L-ascorbic acid instability in solution remains unsolved for the practical delivery of effective levels of L-ascorbic acid in topical, personal care products.

SUMMARY OF THE INVENTION

It is an object of the present invention to provide stable supersaturated ascorbic acid solutions, and compositions incorporating such solutions.

It is another object of the present invention to provide such solutions that comprise from about 0.15 wt. % to about 25 wt. % ascorbic acid dissolved in a polyol vehicle.

It is still another object of the present invention to provide a method of preparing stable solutions of L-ascorbic acid and stable solutions of isomeric forms of ascorbic acid (hereinafter referred to collectively as "ascorbic acid"), at therapeutically significant concentrations.

It is a further object of the present invention to provide such a method of achieving chemical stability of ascorbic acid in solubilized form at therapeutically significant concentrations.

It is a still further object of the present invention to provide such a method of making supersaturated solutions of ascorbic acid in polyols, which solutions are stable over time, temperature changes and other environmental factors.

These and other objects will become apparent to those skilled in the art after having the benefit of the present invention.

To accomplish the foregoing objects and advantages, the present invention, in brief summary, is a stable, supersaturated solution of from about 0.15 to about 25 pecent by weight (wt. %), preferably from about 10 wt. % to about 25 wt. %, most preferably from about 10 wt. % to about 15 wt. %, of ascorbic acid in a polyol vehicle. In addition, the present invention comprises a method of preparing a stable, supersaturated solution of ascorbic acid in a polyol vehicle, comprising the steps of (a) heating the polyol vehicle to an elevated temperature of about 75° C. to about 130° C., preferably from about 75° C. to about 100° C., and (b) dissolving from about 0.15 to about 25 percent by weight (wt. %), preferably from about 10 wt. % to about 25 wt. %, most preferably from about 10 wt. % to about 15 wt. %, of ascorbic acid in the heated polyol vehicle.

DETAILED DESCRIPTION OF THE PREFERRED EMBODIMENT

In the present invention, a polyol vehicle is used to form a stable, supersaturated ascorbic acid solution, hereinafter referred to as an ascorbic acid/polyol solution.

It was discovered that when a polyol vehicle is heated to about 85° C. to about 95° C., the polyol vehicle is able to dissolve up to about 25 wt. % of ascorbic acid. Surprisingly, the polyol vehicle continues to hold such high concentrations of ascorbic acid in solution even when cooled back to ambient temperatures (approximately 20° C. to 25° C.). Even more surprising, such polyol/ascorbic acid solutions hold below 0° C. without precipitating the ascorbic acid.

A "polyol" is defined herein as a compound with at least two hydroxyl groups per molecule, i.e. a compound having multiple hydroxyl groups as part of its molecular structure.

A subclass of polyols is polyhydric alcohols. Examples of polyols suitable in the present invention include polyhydroxy-alcohols such as, for example, glycerin, propylene glycol, butylene glycol, polyethylene glycol, polypropylene glycol, polyoxyethylene glycol, polyoxypropylene glycol and the like, or mixtures thereof; mannitol, sorbitol, the hydroxysilicones, sucrose, glucose, dextrose, trehalose, and structural and functional derivatives of such polyols, as well as carbohydrates with one or more additional substituent hydroxyl groups.

The solubility of ascorbic acid in the selected polyol is proportional to the molar density of hydroxyl groups that make up the polyol. Consequently, glycerin is a better solvent for ascorbic acid relative to propylene glycol. Also, the order of increasing ascorbic acid solubility is butylene glycol is less than propylene glycol which is less than glycerin.

The polyol vehicle can comprise from about 75 to about 99.85 wt. % of the ascorbic acid/polyol solution. Preferably, the polyol vehicle is from about 75 wt. % to about 95 wt. %, based on the combined weight of the ascorbic acid and polyol vehicle.

The ascorbic acid can include one selected from the group consisting of L-ascorbic acid, D-ascorbic acid, D-araboascorbic acid, L-araboascorbic acid and combinations thereof. Preferably, the ascorbic acid is L-ascorbic acid. However, as stated above, it can be a sterioisomer of L-ascorbic acid, such as D-ascorbic acid, D-araboascorbic acid (also known as erythorbic acid) and L-araboascorbic acid. The ascorbic acid can comprise about 0.15 wt. % to about 25 wt. % of the ascorbic acid/polyol vehicle solution. To be effective, a composition containing the ascorbic acid/polyol solution in combination with other ingredients should contain at least about 5 wt. % ascorbic acid based on the total weight of the composition (the ascorbic acid/polyol solution plus all other ingredients).

Pursuant to the present invention, ascorbic acid remains solubilized at supersaturation levels for extended periods of time and does not appreciably degrade under conditions that would quickly destroy ascorbic acid in other vehicles. For example, a 20 wt. % L-ascorbic acid/polyol solution prepared pursuant to the present method holds without precipitation or degradation for months at 43° C. or 110° F. In the same fashion, stable supersaturated solutions in polyols of other sterioisomers of L-ascorbic acid, such as D-ascorbic acid, D-araboascorbic acid and L-araboascorbic acid, were successfully made.

The supersaturated ascorbic acid/polyol solution prepared according to the method of this invention can be incorporated into any composition intended for either topical or ingestible use in any cosmetic, dermatological or pharmaceutical utility. The ascorbic acid/polyol solution can be readily used in compositions containing other cosmetic and pharmaceutical agents, e.g., anti-fungals, vitamins, sunscreens, retinoids, antihistamines, depigmenting agents, anti-inflammatory agents, anesthetics, surfactants, emulsifiers, stabilizers, preservatives, antiseptics, emollients, thickeners, lubricants, humectants, chelating agents, fragrances, colorants and skin penetration enhancers.

Compositions containing the ascorbic acid/polyol solution may also contain one or more alcohol co-solvents, such as ethanol, and one or more emulsifiers. The emulsifier can be anionic, nonionic, cationic or amphoteric or a combination thereof. A nonionic emulsifier is preferred. Examples of nonionic emulsifiers are commercially available sorbitans, alkoxylated fatty alcohols, e.g. Brij 78™, and alkyl polyglycosides. Examples of anionic emulsifers may include soaps, alkyl sulfates, monoalkyl and dialkyl phosphates, alkyl sulphonates and acyl isethionates. Examples of cationic emulsifiers are quarternium salts, cetrimonium chloride and laurtrimonium chloride. Examples of amphoteric emulsifiers include cocamidopropyl betaine, coco betaine, myristamidopropyl betaine and oleyl betaine. Other suitable emulsifers are described in literature such as in McCutcheon's *Detergents and Emulsifiers*, North American Ed., pages 317–324 (1986), incorporated herein by reference.

A preservative can be used in compositions containing the ascorbic acid/polyol solution. Preservatives suitable for use with the ascorbic acid/polyol solution of this invention include parabens, sorbates, benzyl alcohol, diazolidinyl urea and isothiazolinones. Preservatives can be present in an amount from about 0.001 wt. % to about 15 wt. % of the total composition.

Such compositions can also contain an emollient. Examples of one or more emollients suitable for use with supersaturated solutions of ascorbic acid in polyols include silicone oils, such as cyclomethicone/dimethicone copolyol and cyclotetramethicone, mineral oil, cocoa butter, shea butter, fatty acids esters, beeswax, petrolatum and lanolin. The emollient is present in an amount from about 5 wt. % to about 50 wt. % of the total composition. Other suitable emollients are described in literature such as in Sagarin, *Cosmetics, Science and Technology*, 2nd Ed., vol. 1, pages 32–43 (1972), incorporated herein by reference.

A thickening agent can be used in compositions containing the ascorbic acid/polyol solution. Examples of thickening agents suitable for use with the ascorbic acid/polyol solution of the present invention include xanthan gum, xanthan gum brine tolerant, hydroxypropyl cellulose, hydroxyethyl cellulose, Carbopol™ and gum acacia. The thickening agent comprises about 0.01 wt. % to about 5 wt. %, preferably about 0.1 wt. % to about 2 wt. %, of the total composition.

A composition containing the ascorbic acid/polyol solution may include from about 1.0 wt. % to about 15 wt. %, preferably from about 5 wt. % to about 10 wt. %, of humectants, such as urea.

The ascorbic acid/polyol solution can also be used in compositions containing about 0.1 wt. % to about 15 wt. %, preferably about 0.5 wt. % to about 5 wt. %, keratolytic agents, such as salicylic acid and benzoyl peroxide; about 0.1 wt. % to about 40 wt. %, preferably about 1 wt. % to about 20 wt. % skin lightening agents, such as kojic acid, benzoquinone and PT-40; about 1.0 wt. % to about 20 wt. %, preferably about 5 wt. % to about 10 wt. %, organic and inorganic sunscreens, such as titanium dioxide, zinc oxide, benzylidene camphor, salicylates, cinnamic acid derivatives and dihydroxy-naphthoic acid and its salts; about 1.0 wt. % to about 10 wt. %, preferably about 5 wt. % to about 10 wt. %, quinoline derivatives, quinine salts, uric and violuric acids, tannic acid and its derivatives, hydroquinone, dioxybenzone, benzoresorcinol, 2,2,4,4-tetrahydroxybenzophenone, etocrylene; about 0.001 wt. % to about 5 wt. %, preferably about 0.1 wt. % to about 2 wt. %, retinoids, such as retinol, retinoic acid, retinyl palmitate, retinyl propionate or retinyl acetate as well as synthetic retinoid mimics; about 0.001 wt. % to about 5 wt. %, preferably about 1 wt. % to about 3 wt. % hormones such as estriol or estradiol; about 1.0 wt. % to about 20 wt. %, preferably about 4 wt. % to about 10 wt. %, alpha-hydroxyacids (e.g. glycolic acid, lactid acid), alpha-keto acids (e.g. pyruvic acid); about 0.1 wt. % to about 50 wt. %, preferably about 2 wt. % to about 20 wt. %, vitamins (e.g. vitamin K, vitamin E, vitamin E acetate); about 0.1 wt. % to about 10 wt. %, preferably about 2 wt. % to about 5 wt. %, antifungals (e.g. clotrimazole, ketoconazole, miconazole, naftifine, tolnaftate); about 0.1 wt. % to about 20 wt. %, preferably about 5 wt. % to about 15 wt. %, self-tanning agents (e.g. dihydorxyacetone, lawsone); about 0.001 wt. % to about 5 wt. %, preferably about 0.5 wt. % to about 2 wt. %, corticosteriods; about 0.001 wt. % to about 5 wt. %, preferably about 0.1 wt. % to about 1.0 wt. %, antibiotics (e.g. erythromycin, tetracyclin, cephalosporins); about 0.01 wt. % to about 60 wt. %, preferably about 1 wt. % to about 20 wt. %, topical analgesics (e.g. lidocane); about 1.0 wt. % to about 15 wt. %, preferably about 5 wt. % to about 10 wt. %, ceramides; about 5 wt. % to about 20 wt. %, preferably about 5 wt. % to about 10 wt. %, essential fatty acids; and about 5 wt. % to about 20 wt. %, preferably about 5 wt. % to about 20 wt. %, ω-hydroxy fatty acids.

The ascorbic acid/polyol solution can also be used in compositions with about 0.01 wt. % to about 5 wt. %, preferably about 0.1 wt. % to about 1.0 wt. %, topical anti-inflammatory agents that reduce inflammation caused by UV exposure, such as steroidal anti-inflammatories and non-steroidal anti-inflammatories. Examples of steroidal and non-steroidal anti-inflammatories can be found in texts, such as Rainsford, *Antiinflammatory and Anti-Rheumatic Drugs*, vols. I–III, CRC Press, Boca Raton, Fla. (1985), which is incorporated herein by reference. Specific examples of other suitable anti-inflammatories include enolic acids, oxicams (e.g. piroxicam, isoxicam), fenamic acid derivatives, meclofenamic acid derivatives (e.g. sodiummeclofenamate), flufenamic acid derivatives (e.g. N-(a,a,a-trifluoro-m-tolyl) anthranilic acid), mefenamic acid derivatives (e.g. N-(2,3-xylyl) anthranilic acid) propionic acid esters, such as ibuprofen, naproxen, benoxaprofen, flubiprofen, ketoprofen, suprofen, of which ibuprofen is most preferred; pyrazolidinediones, such as feprazone, trimethasone, oxyphenbutazone, sulfinpyrazone, phylbutaxone; acetic acid derivatives, such as diclofenac, fenclofenac, indomethacin, sulindac, tolmetic, isoxepac, furofenac, clidanac, zomepirac acematicin, of which indomethacin is most preferred; and salicylic acid derivatives, such as aspirin, safaprin, disalacid, benorylate and trisilate.

Compositions containing the ascorbic acid/polyol solution of the present invention may also include from about 0.5 wt. % to about 30 wt. %, preferably from about 1 wt. % to about 25 wt. % of the total composition, safe anti-inflammatory products of natural origin shown to possess anti-inflammatory activity. Those skilled in the art will recognize among such agents, aloe vera extracts, extracts from genus Rubis (*Rubia Cordifolia*), extracts from genus Commiphom (*commphora Mukul*), willow bark, matricarria flowers, arnica flower, comfrey root, fenugreek seed, and the like.

The ascorbic acid/polyol solution can also be used in compositions that contain from about 0.1 wt. % to about 20 wt. %, preferably from about 1.0 wt. % to about 15 wt. % of the total composition, antioxidants with phenolic hydroxy functions, such as gallic acid derivatives (e.g. propyl gallate), bioflavonoids (e.g. quercetin, rutin, daidzein, genistein), ferrulic acid derivatives (e.g. ethyl ferrulate, sodium ferrulate), and 6-hydroxy-2,5,7,-tetramethylchroman-2-carboxylic acid. The compositions may also contain effective concentrations of water-soluble antioxidants, such as uric acid, reductic acid and tannic acid. Other possible antioxidants that the composition may contain are those which have one or more thiol (-SH) functions in either reduced or non-reduced form such as glutathione, lipoic acid, thioglycolic acid and thiolactic acid. The composition may also include inorganic antioxidants, such as sulfites, bisulfites, metbisulfite or other inorganic salts and acids containing sulfur in oxidation state +4.

The ascorbic acid/polyol solution can also be used in compositions that contain about 0.01 wt. % to about 50 wt. %, preferably about 1.0 wt. % to about 30 wt. % of the total composition, insect repellents, such as DEET®, other aliphatic, cyclic or aromatic amides, citronella oil, terpineol, cineole, neem oil, terephthalic acid and its esters. Other suitable insect repellents can be found in Technical Bulletin No. 1549 of the U.S. Department of Agriculture or in the USDA Agricultural Handbooks No. 461, 69 and 340, which are incorporated herein by reference.

The ascorbic acid/polyol solution can also be used in compositions that contain about 0.01 wt. % to about 30 wt. %, preferably about 1.0 wt. % to about 15 wt. % of the total composition, skin cooling compounds, such as menthol, methyl glycerol, asymmetrical carbonates, thiocarbonates and urethanes, N-substituted carboxamides, ureas or phosphine oxides as described in *J. Cosmet. Chem.*, vol. 29, page 185 (1978) and incorporated herein by reference, methyl lactate and menthone glycerin acetal.

The ascorbic acid/polyol solution of the present invention can also be dispersed as droplets in the oil phase of a multiphase emulsion composition, such as water-in-oil-in-water type disclosed in U.S. Pat. No. 4,254,105 to Fukuda, incorporated herein by reference. The ascorbic acid/polyol solution of the invention can also be provided as a component of the oil phase of a triple emulsion of the oil-in-water-silicone fluid type as disclosed in U.S. Pat. No. 4,960,764 to Figueroa, Jr. et al., incorporated herein by reference.

The ascorbic acid/polyol solution of the present invention can be made as a liposomal formulation, for example, according to the methods described in Mezei, *J. Pharm. Pharmacol.*, vol. 34, pages 473–474 (1982), incorporated herein by reference. In such compositions, the droplets of the ascorbic acid/polyol solution can be entrapped inside the liposomal vesicles and then incorporated into the final formula in such a form. The shell of the liposome can be a phospholipid but can be replaced with other suitable lipids (e.g. skin lipids) as would be evident to those skilled in the art. The liposomes can then be added to any of the carrier systems described herein as explained in Mezei, *Liposomes as Skin Drug Delivery System, Topics in Pharmaceutical Sciences*, Breimer Speiser, Eds., pages 345–358, Elsevier Science Publishers B. V., New York (1985), incorporated herein by reference, or according to the reverse-phase evaporation method described in *Proc. Nat'l. Acad. Sciences*, vol. 75, pages 4194–4198 (1978), and *J. Soc. Cosm. Chem.*, vol. 43, pages 93–100 (1992), both of which are incorporated herein by reference. One skilled in the art can adapt any other similar, hollow polymeric particle having structural or functional properties similar to those of liposomes and achieve results equivalent to those taught herein.

The stable, supersaturated solutions of ascorbic acid in a polyol or the ascorbic acid/polyol solution can also be entrapped in polymeric vesicles with a shell consisting of a suitable polymeric material, such as gelatin, cross-linked gelatin, polyamide, polyacrylates and the like. Such vesicles can then be incorporated into any cosmetic formulation.

EXAMPLE 1

A lotion according to the present invention was made with the following, expressed as percents of total weight of the entire lotion composition:

| Ingredient | Function | wt. % |
| --- | --- | --- |
| Polyethylene glycol | polyol solvent | 3.90% |
| Glycerin | polyol solvent | 60.00% |
| Carbopol ™ 940 | thickener | 0.10% |
| Propylene glycol | polyol solvent | 5.00% |
| Ethanol | co-solvent | 15.00% |
| L-Ascorbic acid | active | 15.00% |
| Salicylic acid | keratolytic agent/ anti-inflammatory | 1.00% |
| Total | | 100.00% |

EXAMPLE 2

A cream according to the present invention was made with the following, expressed as percents of total weight of the cream composition:

| Ingredient | Function | wt. % |
| --- | --- | --- |
| Glycerin | polyol solvent | 50.00% |
| L-Ascorbic Acid | active | 12.50% |
| Brij 78 ™ | solubilizer | 1.50% |
| Cyclomethicone/ Dimethicone Copolyol | emollient | 12.50% |
| Shea Butter | emollient | 2.50% |

-continued

| Ingredient | Function | wt. % |
|---|---|---|
| Petrolatum | emollient | 2.50% |
| Cyclotetramethicone | emollient | 18.50% |
| Total | | 100.00% |

The present invention has been described with particular reference to the preferred forms thereof. It will be obvious that various changes and modifications may be made therein without departing from the spirit and scope of the present invention as defined by the following claims.

What is claimed is:

1. A method of forming a stable, supersaturated solution of ascorbic acid encapsulated in a vesicle, comprising the steps of:
   (a) heating a polyol vehicle to an elevated temperature above 75° C.;
   (b) dissolving ascorbic acid in said polyol vehicle in an amount from about 0.15 wt. % to about 25 wt. % based on a combined weight of said ascorbic acid and said polyol vehicle, wherein said solution is free of precipitated ascorbic acid; and
   (c) entrapping said solution inside a vesicle.

2. The method according to claim 1, wherein said ascorbic acid is selected from the group consisting of L-ascorbic acid, D-ascorbic acid, D-araboascorbic acid, L-araboascorbic acid and mixtures thereof.

3. The method according to claim 1, wherein said elevated temperature is about 85° C. to about 95° C.

4. The method according to claim 1, wherein from about 10 wt. % to about 25 wt. % of said ascorbic acid is dissolved in said polyol vehicle.

5. The method according to claim 1, wherein said polyol vehicle is selected from the group consisting of glycerin, propylene glycol, butylene glycol, polyethylene glycol, polypropylene glycol, polyoxyethylene glycol, polyoxypropylene glycol, sucrose, glucose, dextrose, trehalose and mixtures thereof.

6. The method according to claim 5, wherein said polyol vehicle is selected from the group consisting of glycerin, propylene glycol, butylene glycol and mixtures thereof.

7. The method according to claim 1, wherein said vesicle is a hollow polymeric particle.

8. The method according to claim 1, wherein said vesicle is a liposomal vesicle entrapping said solution.

9. A stable, supersaturated solution of ascorbic acid encapsulated in a vesicle formed by:
   (a) heating a polyol vehicle to an elevated temperature above about 75° C.;
   (b) dissolving ascorbic acid in said polyol vehicle in an amount from about 0.15 wt. % to about 25 wt. % based on a combined weight of said ascorbic acid and said polyol vehicle, wherein said solution is free of precipitated ascorbic acid; and
   (c) entrapping said solution inside a vesicle.

10. The solution according to claim 9, wherein said ascorbic acid is selected from the group consisting of L-ascorbic acid, D-ascorbic acid, D-araboascorbic acid, L-araboascorbic acid and mixtures thereof.

11. The solution according to claim 9, wherein said elevated temperature is about 85° C. to about 95° C.

12. The solution according to claim 9, comprising about 10 wt. % to about 25 wt. % of said ascorbic acid.

13. The solution according to claim 9, wherein said polyol vehicle is selected from the group consisting of glycerin, propylene glycol, butylene glycol, polyethylene glycol, polypropylene glycol, polyoxyethylene glycol, polyoxypropylene glycol, sucrose, glucose, dextrose, trehalose and mixtures thereof.

14. The solution according to claim 13, wherein said polyol vehicle is selected from the group consisting of glycerin, propylene glycol, butylene glycol and mixtures thereof.

15. A composition comprising the solution of claim 9, and at least one ingredient selected from the group consisting of an anti-inflammatory agent, a sunscreen agent, an antioxidant, a chelating agent, a humectant, an emulsifier, a surfactant, an insect repellent, an anesthetic, an antimicrobial agent, a keratolytic agent, an exfoliating agent and an anti-acne agent.

16. The composition of claim 15, wherein said ascorbic acid of said supersaturated solution of ascorbic acid comprises at least 5 wt. % of said composition.

17. A stable, supersaturated solution encapsulated in a vesicle comprising from about 10 wt % to about 25 wt % ascorbic acid dissolved in a polyol vehicle, wherein said solution is free of precipitated ascorbic acid.

18. The solution according to claim 17, wherein said ascorbic acid is selected from the group consisting of L-ascorbic acid, D-ascorbic acid, D-araboascorbic acid, L-araboascorbic acid and mixtures thereof.

19. The solution according to claim 17, wherein said polyol vehicle is selected from the group consisting of glycerin, propylene glycol, butylene glycol, polyethylene glycol, polypropylene glycol, polyoxyethylene glycol, polyoxypropylene glycol, sucrose, glucose, dextrose, trehalose and mixtures thereof.

20. The method according to claim 1, further comprising the step of:
   (d) adding said supersaturated ascorbic acid solution encapsulated in a vesicle to a composition comprising at least one ingredient selected from the group consisting of an anti-inflammatory agent, a chelating agent, an insect repellent, an anesthetic, an exfoliating agent, a skin lightening agent, a keratolytic agent, an antibiotic, an alpha hydroxy fatty acid, and an antioxidant selected from the group consisting of a phenolic antioxidant, a water-soluble antioxidant, a thiol function containing antioxidant, and an inorganic antioxidant.

21. The method according to claim 20, wherein said antioxidant is selected from the group consisting of a gallic acid derivative, bioflavonoid, a ferrulic acid derivative, 6-hydroxy-2,5,7,-tetramethylchroman-2-carboxylic acid, uric acid, reductic acid, tannic acid, glutathione, lipoic acid, thioglycolic acid, thiolactic acid, a sulfite, a bisulfite, a metbisulfite, a sulfur containing inorganic salt in the oxidation state of +4, a sulfur containing inorganic acid in the oxidation state of +4, and mixtures thereof.

* * * * *